(12) United States Patent
Ivey et al.

(10) Patent No.: US 7,100,841 B2
(45) Date of Patent: Sep. 5, 2006

(54) FRAGRANCE DISPENSER CAPILLARY PUMP

(75) Inventors: Ellwood G. Ivey, Savannah, GA (US); Cedric Stratton, Savannah, GA (US)

(73) Assignee: Tri Senx Holdings, Inc., Savannah, GA (US)

( * ) Notice: Subject to any disclaimer, the term of this patent is extended or adjusted under 35 U.S.C. 154(b) by 0 days.

(21) Appl. No.: 09/900,416

(22) Filed: Jul. 6, 2001

(65) Prior Publication Data

US 2003/0006302 A1 Jan. 9, 2003

(51) Int. Cl.
*B05B 1/24* (2006.01)

(52) U.S. Cl. .................. 239/136; 239/135; 239/302; 392/394; 392/406; 222/146.5

(58) Field of Classification Search .............. 239/302, 239/128, 135, 136; 392/386, 394, 403, 406, 392/395; 222/146.1, 146.2, 146.5
See application file for complete search history.

(56) References Cited

U.S. PATENT DOCUMENTS

| | | | | |
|---|---|---|---|---|
| 3,851,146 A | * | 11/1974 | Bennett | 239/136 |
| 4,219,725 A | * | 8/1980 | Groninger | 239/136 |
| 4,260,873 A | * | 4/1981 | Simmonds | 239/136 |
| 4,771,563 A | * | 9/1988 | Easley | 239/136 |
| 5,095,647 A | * | 3/1992 | Zobele et al. | 239/135 |
| 5,484,086 A | * | 1/1996 | Pu | 392/406 |
| 6,145,241 A | * | 11/2000 | Okuno | 239/136 |
| 6,169,852 B1 | * | 1/2001 | Liao et al. | 392/395 |

* cited by examiner

*Primary Examiner*—Stephen J. Ganey
(74) *Attorney, Agent, or Firm*—John L. James

(57) ABSTRACT

A capillary pump for a fragrance dispenser has a reservoir for holding fragrance oil. The reservoir is capped with a silicone rubber cap with a vapor port therein for emitting vaporized fragrance oil. A capillary tube has its bottom end extending to the bottom of the reservoir where capillary action draws fragrance oil up into the capillary tube. A heating element inside the capillary tube vaporizes fluid drawn into the tube. Electrical leads for the heating element exit through the silicone rubber cap. The cap, capillary tube and heating element form a unit for insertion of the capillary tube and heating element into the reservoir.

19 Claims, 2 Drawing Sheets

FRAGRANCE DISPENSER CAPILLARY PUMP

CROSS REFERENCE TO RELATED APPLICATIONS

This application is related to applicant's cofiled application Ser. Nos. 0901-01-307, 09/900,430.

FIELD OF THE INVENTION

The present invention relates to a device for dispensing a fragrance or deodorizer for improving the air quality in a home, automobile, building or other closed space.

BACKGROUND OF THE INVENTION

The air in a room in a home or other building becomes stale when the air remains stagnant. Air is often stagnant during periods when the ventilation is idle. Such idle periods occur when the desired temperature is achieved and heating or cooling is no longer required. This is particularly true in a home ventilation system where the blower only operates when heating or cooling is needed to conserve energy. In many areas during autumn and spring, heating or cooling is not needed at all in the home or needed for only brief periods of time contributing to stale air. Where the blower operation is adequate to keep the air circulating and filtered, the air can still be less than pleasant because of odors from cooking, smoking or other activities. Without the benefit of adequate air filtration, odors from cooking and smoking can settle on drapes and carpets making the undesirable odors ever present.

Sometimes it is desirable to create an aroma in a room for a special occasion or for a particular season. For example, during the winter holiday season, a pine fragrance enhances the holiday tree and decorations making for a more festive occasion. Similarly, a nutmeg or spice aroma enhances the thanksgiving holiday season because the aroma hints of pumpkin pie and other good things to eat. It is now recognized that certain fragrances invoke or enhance certain moods or reactions in people. The use of fragrances to create or alter moods is known as aroma therapy. Home aroma therapy has heretofore used scented candles or hand held sprays. Both require user intervention requiring the user to intentionally start the therapy which is not realistic when the person is not in a good mood. Also, candles could present a burn or fire hazard to an irritable person. It is desirable to have a fragrance dispenser that operates automatically to dispense fragrance for aroma therapy and special occasions and situations. It is also desirable to have a single fragrance dispenser that can deliver more than one fragrance.

Automobiles also present an opportunity for odors. Odors are created from merely using an automobile, and while eating or smoking. While these odors can be controlled by not eating or smoking in the automobile, there are odors over which the occupants have no control. Odors are created in the ventilation system where there is a moist environment for microorganisms to thrive. They grow because of the moisture created by the air conditioning system. It is impossible for an automobile owner to clean the air conditioning system because disassembly is required. It is therefore desirable to have an air freshener that is easy to use and effective in an automobile.

Fragrance dispensers are now available in a variety of configurations, but are limited in their effectiveness because the fragrance substance used to impart the aroma is not present in its most concentrated form; that is, these devices do not use the concentrated fragrance oils as they come from the manufacture. The oils are diluted with alcohol or mixed with a binder to slow evaporation. When the delivery device is a canister with a spray nozzle, the fragrance oil is diluted with alcohol so that a spray develops without clogging the nozzle. When the delivery device is a plug-in unit, the fragrance oil is mixed with a binder so that fragrance is only released when the electric current is applied. It is desirable to have a delivery device that uses the fragrance substance in its concentrated form for maximum effectiveness and longest life per unit volume of fragrance substance.

Another problem with conventional delivery devices is that the strength of the aroma is not constant over the life of the fragrance substance. A fragrance substance mixed with other materials does not always remain uniformly mixed causing uneven amount of fragrance to be emitted. Also, the evaporation rates of the fragrance substance and binder may differ causing uneven fragrance to be emitted. This is particularly true as the substance is depleted causing the aroma strength to weaken as the substance is consumed. Accordingly, it will be appreciated that it would be highly desirable to have an aroma delivery system that provides constant aroma strength as the fragrance substance is consumed.

SUMMARY OF THE INVENTION

Briefly summarized, according to one aspect of the present invention, a fragrance dispenser capillary pump comprises a housing having a bottom and a sidewall with the bottom and sidewall forming a reservoir. A silicone rubber cap has a vapor port and is attached to a top portion of the sidewall. A vitreous capillary tube is positioned in the housing so that the bottom end of the tube extends into the reservoir near the bottom to draw fluid from the reservoir up into the capillary tube. A heating element in the form of a coiled heater wire inside the capillary tube vaporizes fluid in the capillary tube forcing the vapor out the vapor port in the cap. Electrical leads extend from the heating element through the silicone rubber cap for connecting to a power source. The cap, capillary tube, heating element and electrical leads form a unitary structure for insertion into the housing.

The reservoir contains a fragrance oil that is drawn up into the tube by capillary action. The fragranced oil is in a concentrated form for imparting maximum aroma into the surrounding via the vapor port. Because it is concentrated, the fragrance oil provides longer life per unit volume of fragrance substance than when its mixed with a solvent or binder. Because the oil is not mixed with a binder or solvent, its strength remains constant thereby providing constant aroma strength until the oil is depleted. The capillary tube reaches to the bottom of the reservoir to effectively use all the oil. The heating element heats oil in the tube causing it to vaporize without heating the oil in the reservoir thereby maximizing the use of energy.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE PREFERRED EMBODIMENTS

Figure 1:
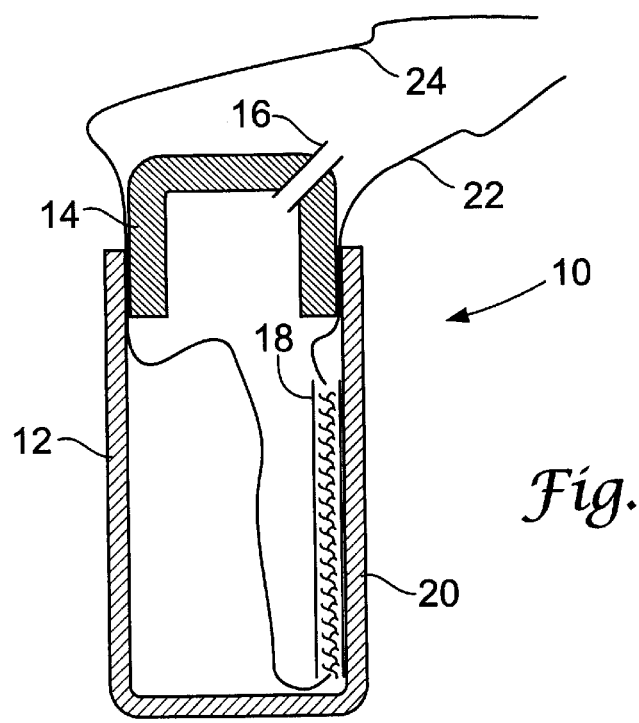
FIG. 1 is a diagrammatic longitudinal sectional view of preferred embodiment of a fragrance dispensing unit according to the present invention.

Referring to FIG. 1, a capillary pump 10 for a fragrance dispenser has a housing 12. The housing 12 is expected to be inserted into a decorative home fragrance dispenser cabinet for use as a stand alone unit or as a plug in unit that plugs into an electrical outlet. The preferred housing material is glass because the fragrance oil is organic in nature and may react with the metals used for metallic containers. A reaction between the fragrance oil and metal may cause the oil to decompose or discolor, and, in a few cases, may catalyze the oil hardening the oil into intractable gels. It is anticipated the reservoir in the housing will be refilled several times before discarding. Where the housing is to be used only once, then metal can be used. The housing may also be constructed of ceramic material.

The housing 12 has a bottom with an upstanding sidewall attached to the bottom. The bottom and sidewall form a reservoir for the fragrance oil. The top of the housing 12 is open to be sealed by an elastomeric cap 14 which has an opening to receive a vapor port 16. Vapor port 16 is preferably a thin, hollow stainless steel tube with an orifice slightly larger than a hypodermic needle, the type used for insulin injections. Vapor port tube 16 need only be about ⅛ inch long. The small metal tube is rapidly heated by vapor as the vapor passes through it. Very little condensation of oil occurs in the short tube prior to emission and dispersion of vapor so that condensation does not cause intermittent sputtering. The emitted substance is thus a true vapor, not a mist of droplets. Being a true vapor, the vaporized oil disperses and fills a room more rapidly and completely than a spray or mist of droplets.

A vitreous capillary tube 18 is positioned upright in the reservoir with its bottom extending to the bottom to substantially empty the reservoir. Glass is preferred for the capillary tube because glass is corrosion resistant. The inner diameter of the tube 18 determines the height to which the fragrance oil is lifted and the size of the heating element 20 inserted therein. Preferably, the reservoir and capillary tube are mutually designed so that the liquid in the capillary tube is within a few millimeters of the top of the tube whether the reservoir is full or near empty. Surface tension provides the pumping action. The capillary tube cannot overflow. The capillary principle is not limited to glass tubes. It also applies to a fibrous bundle which also uses surface tension to elevate liquids, like a wick. A fibrous bundle can draw liquids to far greater heights than a single glass tube thereby allowing deeper reservoirs without loss of efficiency when near empty. A single glass tube has the advantage of being faster acting than a fibrous bundle in that it is almost instantaneous. Thus, where rapid dispensing or continuous operation is a concern, a glass tube is preferred.

The application of heat need not come from a direct contact electric coil. If the capillary tube were a fibrous bundle, a hot air jet would be just as effective. This would be a simple way to dispense fragrances. The wick would be precharged at all times. If covered with a small cap, inadvertent evaporation would not occur, and no oil would be vaporized until ready. If the cap is lifted by the air jet, the same electrical current would run the fan and heat the air. They would be mutually proportionate if energy would fluctuate. This would allow battery operation. Also, this design has only one independent moving part—the fan. The cap could be a passive hinged flap. The heat source would be isolated from the oil which would reduce both the chance of thermal decomposition and the potential for oil ignition.

The heating element 20 is a piece of heater wire, preferably coiled, and positioned inside the capillary tube 18. Heater wire 20 may extend substantially the length of the tube. In the tube heater 20 rapidly brings the oil to a boil causing vapors to rise in the tube and exit into the reservoir chamber above the liquid level where the vapor exits through the vapor port tube 16. It is not necessary for the heater to extend the entire length of the tube. It can exist above the fluid level of the reservoir where it still will vaporize oil in the capillary tube. Because the heater is in direct contact with the oil, the oil in the tube heats rapidly while the oil temperature in the reservoir is essentially undisturbed. Where rapid repeated operation is needed, it is preferable to have the heater coil extend substantially the entire length of the tube to promote cooling between operations.

It is to be noted that the capillary tube need not be positioned inside the reservoir. It could operate just as effectively if placed outside the reservoir. Because the capillary tube is thin, an outside capillary tube may need support. An outside capillary tube could also be wound with an external coil thereby separating the oil from direct heat and electricity.

Figure 2:
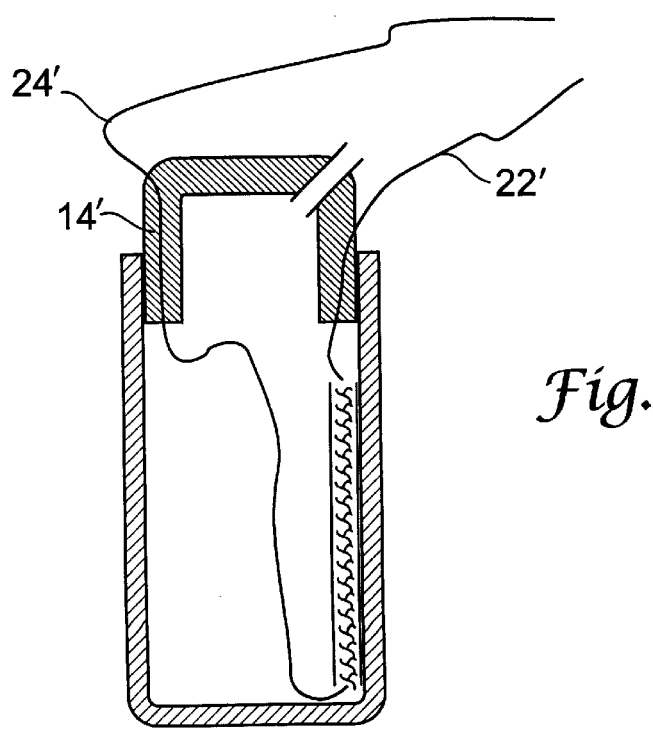
FIG. 2 is a diagrammatic longitudinal sectional view of a fragrance dispensing similar to FIG. 1 but illustrating another preferred embodiment.

Still referring to FIG. 1, the heater coil 20 has upper and lower electrical leads 22, 24 that exit the housing between the sidewall and silicone rubber cap 14. The electrical leads 22, 24 are preferably attached to the rubber cap 14 so that the cap 14, capillary tube 18, heating element 20 and electrical leads 22, 24 form a unit that is easily insert into the housing 12. Where leads 22, 24 are merely attached to the surface of the rubber cap 14, a grommet or extra sealing member are not required because the rubber cap deforms to seal the wires and reservoir as it is inserted into the top of the sidewall of the housing. Obviously, where leads 22, 24 are embedded in the surface, no additional seal is needed. FIG. 2 illustrates a capillary pump with electrical leads 22', 24' deeply embedded in the silicone rubber cap 14'.

Figure 3:
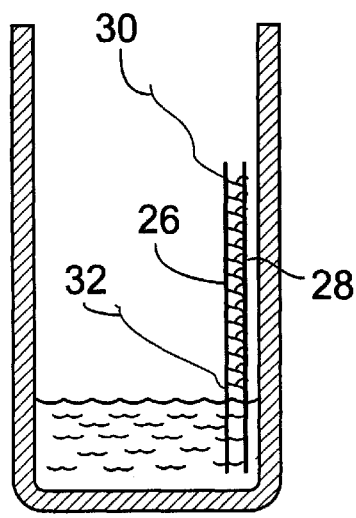
FIG. 3 is a diagram illustrating a heating element coiled outside a capillary tube.

Referring to FIG. 3, a capillary tube 26 has a lower portion immersed in fluid in the reservoir to draw fluid from the bottom of the reservoir while its upper portion extends in the reservoir above the fluid level. A heater wire is 28 coiled about the exterior of the tube 26. Both upper and lower electrical leads 30, 32 are above the fluid level. When energized, the heater coil 28 only heats the oil that is drawn up into the tube. Drawing fluid from the bottom of the reservoir prevents voids that may cause hot spots along the heater wire.

Figure 4:
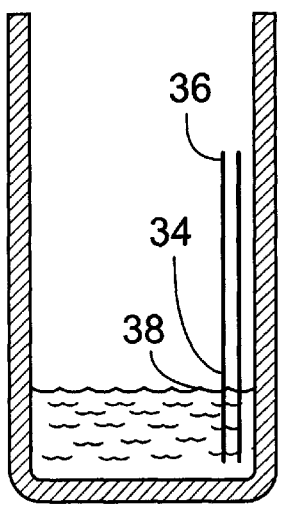
FIG. 4 is a diagram illustrating a heating attached to the outside of a metal capillary tube.

Referring to FIG. 4, a capillary tube 34 has a lower portion immersed in fluid in the reservoir while it upper portion extends in the reservoir above the fluid level. The upper portion is a heating element. Both upper and lower electrical leads 36, 38 are above the fluid level. When energized, the heating element only heats the oil that is drawn up into the tube. Because heating occurs rapidly, little heat is lost to the bottom portion of the tube and to the fluid in the reservoir.

Figure 5:
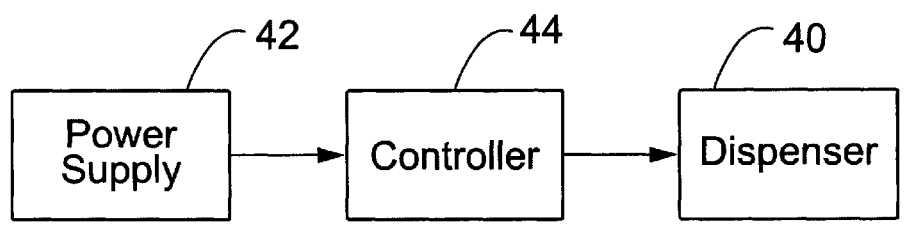
FIG. 5 is a block diagram of a dispensing device with power supply and controller.

Referring to FIG. 5, a fragrance dispenser 40 is connected to a power supply 42 via a controller 44. Such a fragrance dispenser is more fully described in cofiled application Ser.

No. 0901-01-307. The controller may be a simple switch that turns the heater on, or may be a timer to facilitate intermittent operation. A timer can be very effective for aroma therapy use. For example, when timed to emit fragrance to fill a room to coincide with coming home from work or scheduled stressful activity, the fragrance dispenser can help promote relaxation. Such use causes a person to joyfully anticipate coming home. Similarly, a timer can help with a romantic or other aroma theme.

It can now be appreciated that a fragrance container for a home fragrance dispenser has been presented. The fragrance container has two basic components. The first component is a housing forming a fluid reservoir, and the second component is the cap, heater and capillary tube unit. The essential oil is sealed in the reservoir by the cap which is a small dome of molded, translucent, colorless silicone rubber. The cap permits full containment of the oil so that evaporated but undischarged condensate can run freely back into the body of oil in the reservoir. The absence of color prevents color from bleeding into the oil which would be aesthetically unappealing if the housing is transparent. Silicone rubber can operate at high temperatures for long periods of time without decomposing itself or material it contacts. The cap permits electrical leads to pass directly through its silicone rubber walls without a need for grommets or other sealing devices. The cap is simply force-fit or wedged into the open top of the sidewall of the housing.

The heating element is preferably a few turns of nichrome heater wire in the form of a very small cylinder. In one embodiment, the reservoir had a capacity on the order of about 1.0 cc and the heater wire cylinder had a length of about 8 mm and a diameter of about 1 mm. Because of capillary action, the heater wire cylinder is always in contact with the fragrance oil. The heater rapidly brings the oil touching it to the boiling point, but, at the same time, preferably operates at about five percent or less of its rated temperature capacity. By using this low temperature capacity, the heater wire will never reach the ignition temperature when the oil no longer covers the heater wire.

The heater is confined within the thin walled glass sleeve of capillary glass tubing that is open at both ends. The tubing is supported by the heater wire and electrical leads. The tube physically isolates the oil being heated and holds that oil in contact with the heater. Only the oil-in-contact is brought to the boiling point; the remainder of the oil in the reservoir is not significantly impacted. The tube and heater leave only enough space for about 2 mg to about 5 mg of oil, which is he oil that undergoes heating. The 2 mg to 5 mg of oil evaporates very rapidly and increases pressure inside the housing. The combination of the capillary tube and coiled heater provides a powerful capillary that continues to provide a full measure of oil vapor even when the reservoir, which may hold a month's supply, nears empty.

When the oil first begins to boil, the cool interior surfaces of the housing condense the first evaporated oil. Freshly condensed oil, still hot, and therefore less dense, lies on top of the bulk of the oil in the reservoir. The hot zone comprises the inner surface of the silicone rubber cap, the sidewall of the housing above the oil level, the air space in the housing and the vapor port. The hot zone includes the inner surface of the cap because the silicon rubber is a poor heat conductor. The housing sidewall above the oil, if metallic, has a small heat capacity, if glass, it has a high heat capacity but a poor heat conductivity. Heat consumption is held to a minimum.

The reservoir may or may not be electrically conductive. If it is conductive, it could be one electrical lead to the heating coil. The coil would not touch the sidewall anywhere but at one chosen point. It would not be a heat insulator. Leakage of heat would result indirectly in condensation of vapors within the reservoir instead of passing into the atmosphere as desired. One electrical lead would have to pass through the cap. If it is nonconductive, it will also be relatively heat insulating but could not be used as an electrical lead. No special care would be needed to keep the coil from touching the sidewall. The two electrical leads could be pinched between the sidewall and cap on closure.

While the invention has been described with particular reference to the preferred embodiments, it will be understood by those skilled in the art that various changes may be made and equivalents may be substituted for elements of the preferred embodiments without departing from invention. For example, the fragrance container may be mounted on a printed circuit board. The cap, vapor port, electrical leads, and capillary tube, all one unit, can be soldered to appropriate terminals of the printed circuit board. A controller and power supply can also be mounted on the board forming a compact assembly. Several capillary pumps can be mounted on the circuit board and operated by a single controller. Such an arrangement would allow any one of several pumps to be used to dispense a single fragrance. In addition, many modifications may be made to adapt a particular situation and material to a teaching of the invention without departing from the essential teachings of the present invention.

As is evident from the foregoing description, certain aspects of the invention are not limited to the particular details of the examples illustrated, and it is therefore contemplated that other modifications and applications will occur to those skilled in the art. For example, the controller can operate several pumps in a sequence or simultaneously to produce outputs from several pumps which blend to form a unique fragrance. The controller can include a microprocessor that can be programmed to operate selected pumps in sequence or selected pumps simultaneously. Also, an audible or visual alarm can be added to warn when battery power is low. It is accordingly intended that the claims shall cover all such modifications and applications as do not depart from the true spirit and scope of the invention.

What is claimed is:

1. A capillary pump for a fragrance dispenser, comprising:
    a housing having a bottom and a sidewall, said bottom and sidewall forming a reservoir;
    a cap having a vapor port and being attached to a top portion of said sidewall;
    a capillary tube having a top end and a bottom end and being positioned in said housing so that said bottom end extends into said reservoir near said bottom to draw fluid from said reservoir up into said capillary tube;
    a heating element associated with said capillary tube for vaporizing fluid in said capillary tube; and
    a first and second electrical leads connected to said heating element, said electrical leads exiting said housing through said cap for connection to a power source, said cap, capillary tube, heating element and electrical leads forming a unitary structure for insertion into said housing.

2. A capillary pump, as set forth in claim 1, wherein said heating element is a heater wire inside said capillary tube.

3. A capillary pump, as set forth in claim 1, wherein said heating element is a heater wire outside of said capillary tube in contact with said capillary tube.

4. A capillary pump, as set forth in claim 1, wherein said heating element is a coiled heater wire inside said capillary tube.

5. A capillary pump, as set forth in claim 1, wherein said heating element is a heater wire coiled about said capillary tube.

6. A capillary pump, as set forth in claim 1, wherein said capillary tube is constructed of a vitreous material.

7. A capillary pump, as set forth in claim 1, wherein wherein said capillary tube is constructed of a ceramic material.

8. A capillary pump, as set forth in claim 1, wherein wherein said capillary tube is constructed of metal.

9. A capillary pump, as set forth in claim 8, wherein said heating element is an upper portion of said metal capillary tube, said first electrical lead being attached to a top portion of the metal capillary tube, said second electrical lead being attached below said first electrical lead to said upper portion of said metal capillary tube, said electrical leads being above the level of fluid in said reservoir.

10. A capillary pump, as set forth in claim 1, wherein said cap is constructed of silicone rubber.

11. A capillary pump, as set forth in claim 1, wherein said cap is constructed of an elastomeric material.

12. A capillary pump for a fragrance dispenser, comprising:
    a housing having a bottom and a sidewall, said bottom and sidewall forming a reservoir;
    an elastomeric cap having a vapor port and being attached to a top portion of said sidewall;
    a capillary tube having a top end and a bottom end and being positioned in said housing so that said bottom end extends into said reservoir near said bottom to draw fluid from said reservoir up into said capillary tube;
    a heating element associated with said capillary tube for vaporizing fluid in said capillary tube; and
    a first and second electrical leads connected to said heating element, said electrical leads exiting said housing between said cap and sidewall for connection to a power source.

13. A capillary pump, as set forth in claim 12, wherein said heating element is a heater wire inside said capillary tube.

14. A capillary pump for a fragrance dispenser, comprising:
    a housing having a bottom and a sidewall, said bottom and sidewall forming a reservoir;
    an elastomeric cap having a vapor port and being attached to a top portion of said sidewall;
    a vitreous capillary tube having a top end and a bottom end and being positioned in said housing so that said bottom end extends into said reservoir near said bottom to draw fluid from said reservoir up into said capillary tube; and
    a heating element inside said capillary tube for vaporizing fluid in said capillary tube.

15. A capillary pump, as set forth in claim 14, wherein said heating element is a heater wire inside said capillary tube.

16. A capillary pump, as set forth in claim 14, wherein said heating element is a coiled heater wire inside said capillary tube.

17. A capillary pump, as set forth in claim 14, wherein said cap is constructed of silicone rubber.

18. A capillary pump, as set forth in claim 14, including:
    a power source for energizing said heating element; and
    electrical leads for connecting said power source to said heating element.

19. A capillary pump, as set forth in claim 18, including control means for controlling power flow from said power source to said heating element for intermittingly energizing said heating element.

* * * * *